(12) United States Patent
Imada et al.

(10) Patent No.: US 9,963,536 B2
(45) Date of Patent: May 8, 2018

(54) PHENOLIC HYDROXYL GROUP-CONTAINING RESIN, PRODUCTION METHOD THEREFOR, PHOTOSENSITIVE COMPOSITION, RESIST MATERIAL, COATING FILM, CURABLE COMPOSITION AND CURED PRODUCT THEREOF, AND RESIST UNDERLAYER FILM

(71) Applicant: DIC Corporation, Tokyo (JP)

(72) Inventors: Tomoyuki Imada, Ichihara (JP); Seiji Kimoto, Ichihara (JP); Shigenobu Kida, Ichihara (JP)

(73) Assignee: DIC Corporation, Tokyo (JP)

( * ) Notice: Subject to any disclaimer, the term of this patent is extended or adjusted under 35 U.S.C. 154(b) by 0 days. days.

(21) Appl. No.: 15/317,257

(22) PCT Filed: May 28, 2015

(86) PCT No.: PCT/JP2015/065392
§ 371 (c)(1),
(2) Date: Dec. 8, 2016

(87) PCT Pub. No.: WO2016/006358
PCT Pub. Date: Jan. 14, 2016

(65) Prior Publication Data
US 2017/0137556 A1 May 18, 2017

(30) Foreign Application Priority Data

Jul. 9, 2014 (JP) ................................ 2014-141417

(51) Int. Cl.
*C08G 8/04* (2006.01)
*C09D 161/06* (2006.01)
*G03F 7/039* (2006.01)
*G03F 7/11* (2006.01)

(52) U.S. Cl.
CPC ............. *C08G 8/04* (2013.01); *C09D 161/06* (2013.01); *G03F 7/039* (2013.01); *G03F 7/11* (2013.01)

(58) Field of Classification Search
None
See application file for complete search history.

(56) References Cited

U.S. PATENT DOCUMENTS

| 6,197,473 | B1 * | 3/2001 | Kihara | G03F 7/0045 |
| | | | | 430/165 |
| 6,271,337 | B1 * | 8/2001 | Lamartine | C08G 8/12 |
| | | | | 528/219 |
| 2010/0047709 | A1 | 2/2010 | Echigo et al. | |
| 2010/0239980 | A1 * | 9/2010 | Okuyama | G03F 7/0382 |
| | | | | 430/281.1 |
| 2012/0171379 | A1 | 7/2012 | Echigo et al. | |
| 2012/0282546 | A1 * | 11/2012 | Takasuka | C07C 41/30 |
| | | | | 430/281.1 |
| 2013/0078569 | A1 * | 3/2013 | Jain | C07C 67/29 |
| | | | | 430/270.1 |
| 2015/0030980 | A1 | 1/2015 | Echigo et al. | |

FOREIGN PATENT DOCUMENTS

| EP | 1767991 A2 * | 3/2007 |
| IN | 2010MU03473 A * | 6/2013 |
| JP | 2010-248368 A | 11/2010 |
| JP | 2012-162474 A | 8/2012 |
| JP | 2013-079369 A | 5/2013 |
| JP | 2013-195497 A | 9/2013 |

(Continued)

OTHER PUBLICATIONS

Eti Dahan et al., "Octamethylcalix[4]arene," J. Org. Chem., vol. 54, 1989, pp. 6003-6004. (cited in the Notice of Reasons for Revocation of a Patent dated Mar. 30, 2017, issued for JP Patent No. 5939450.).
Dian-Kul Fu et al, "3-Methylcalix[4]arene: A New Versatile Precursor to Inherently Chiral Calix[4]arenes," J. Org. Chem., vol. 61, 1996, pp. 802-804. (cited in the Notice of Reasons for Revocation of a Patent dated Mar. 30, 2017, issued for JP Patent No. 5939450.).
Mitsuru Ueda, "New development of photoresist material development," CMC Publishing Co., Ltd., Aug. 12, 2009, pp. 214-223, information sheet, and partial machine translation. (cited in the Notice of Reasons for Revocation of a Patent dated Mar. 30, 2017, issued for JP Patent No. 5939450.).

(Continued)

*Primary Examiner* — Cynthia Hamilton
(74) *Attorney, Agent, or Firm* — Locke Lord LLP

(57) ABSTRACT

Disclosed are a phenolic hydroxyl group-containing resin which has excellent alkali developing properties and makes it possible to exhibit high heat resistance in a cured product obtained therefrom, a production method therefor, a photosensitive composition, a resist material, a coating film, a curable composition and a cured product thereof, and a resist underlayer film.
A phenolic hydroxyl group-containing resin, including a compound (A) having a molecular structure represented by the following Structural Formula (1).

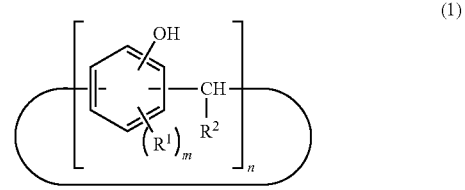

(In the formula, $R^1$ represents an alkyl group, an alkoxy group, or an aryl group, $R^2$ represents a hydrogen atom, an alkyl group, or an aryl group, m is an integer of 1 to 3, and n is an integer of 2 to 15. In the case where m is 2 or more, plural $R^1$'s may be the same as or different from each other.)

20 Claims, 3 Drawing Sheets

(56) References Cited

FOREIGN PATENT DOCUMENTS

JP          2014-227464 A    12/2014
WO          2008/053974 A1   5/2008

OTHER PUBLICATIONS

Tsuguo Yamaoka, "New resist materials and nanotechnology," CMC Publishing Co., Ltd., Sep. 30, 2002, pp. 46-49, information sheet and partial machine translation. (cited in the Notice of Reasons for Revocation of a Patent fated Mar. 30, 2017, issued for JP Patent No. 5939450.).
Notice of Reasons for Revocation of a Patent dated Mar. 30, 2017, issued for JP Patent No. 5939450, No English translation here.
Written Opposition to the Grant of Patent dated Dec. 15, 2016 for JP Patent No. 5939450, No English translation here.
International Search Report dated Aug. 25, 2015, issued for PCT/JP2015/065392.

\* cited by examiner

[Fig. 1]
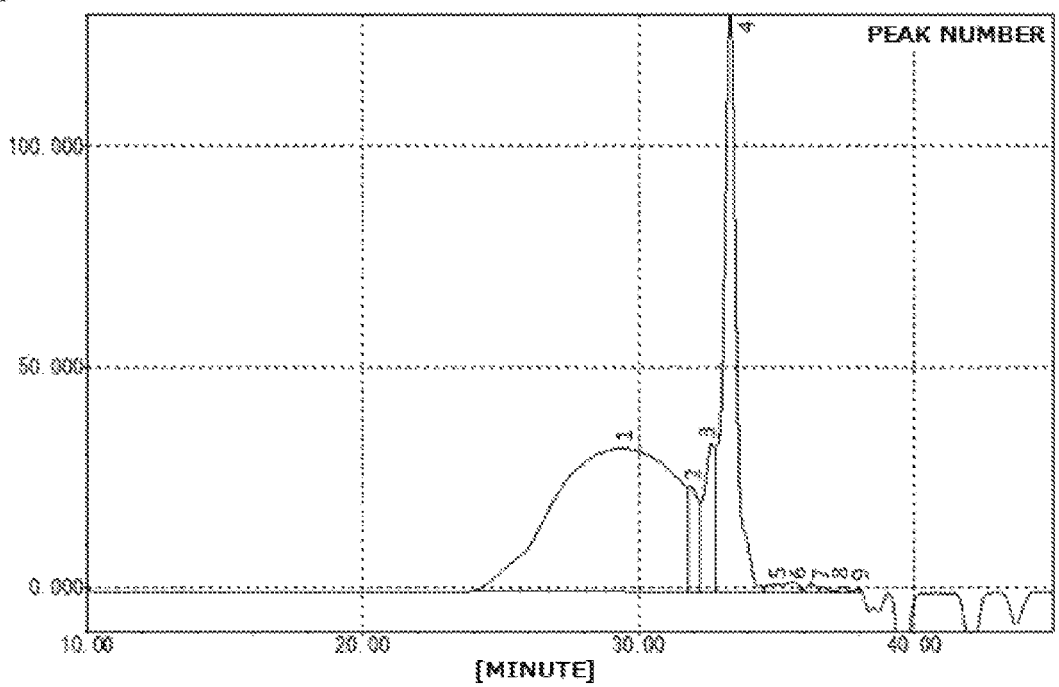

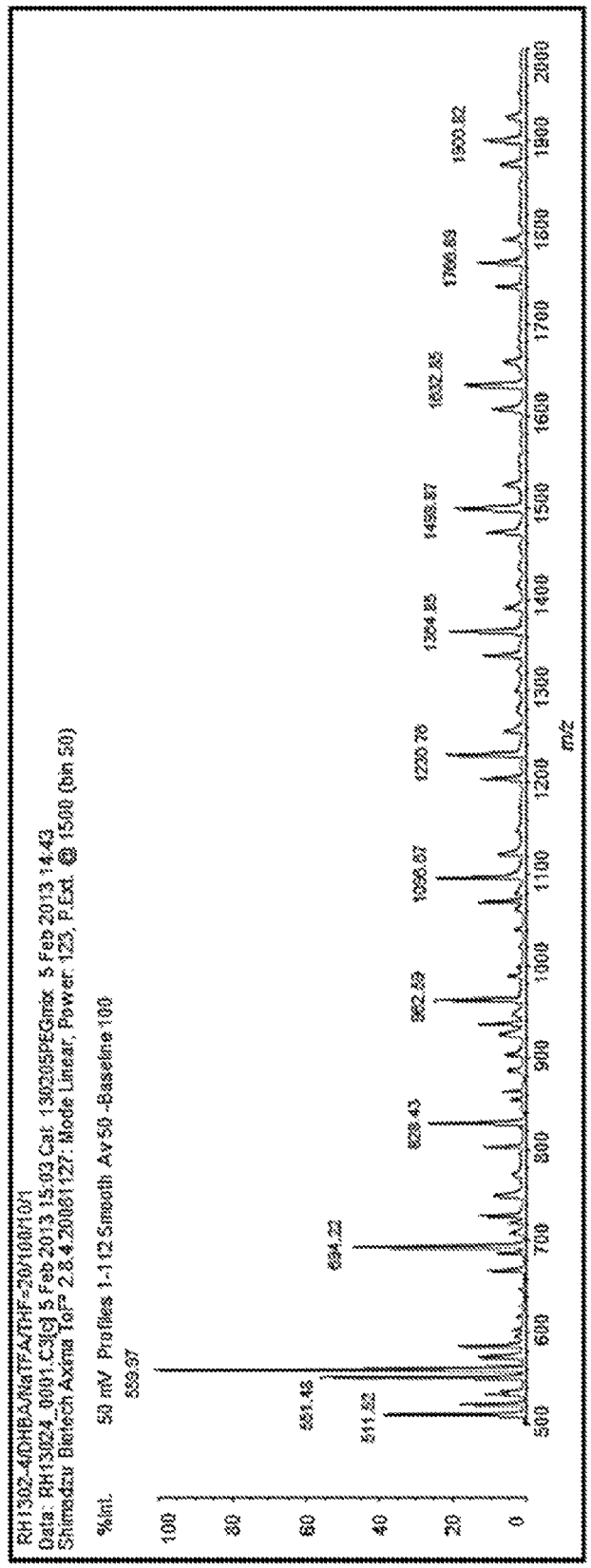
[Fig. 2]

[Fig. 3]
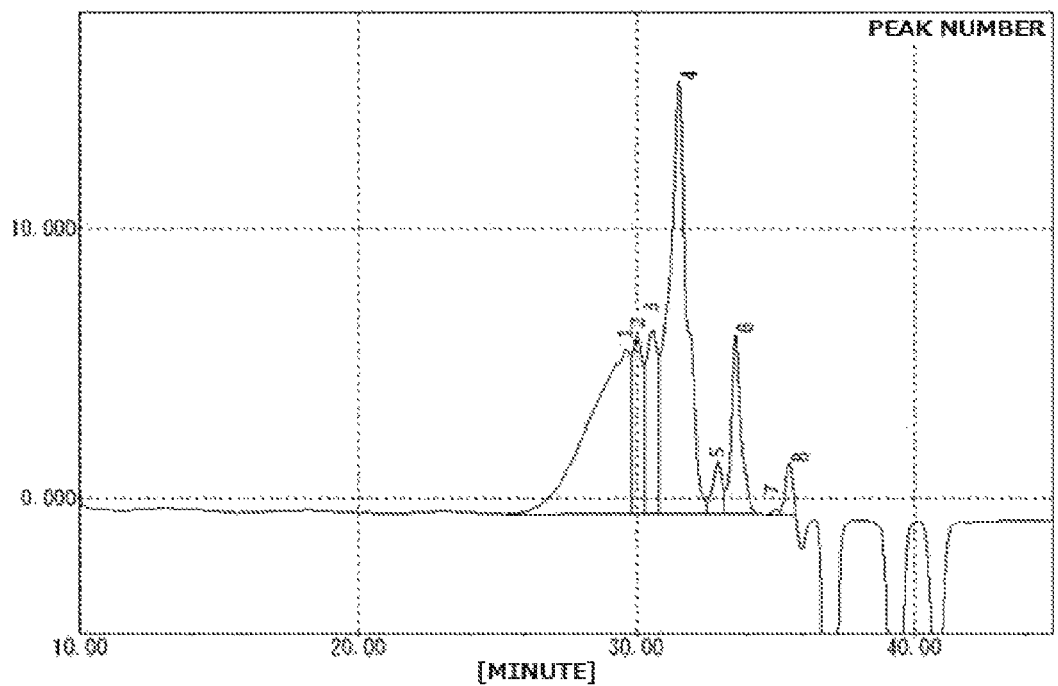

PHENOLIC HYDROXYL GROUP-CONTAINING RESIN, PRODUCTION METHOD THEREFOR, PHOTOSENSITIVE COMPOSITION, RESIST MATERIAL, COATING FILM, CURABLE COMPOSITION AND CURED PRODUCT THEREOF, AND RESIST UNDERLAYER FILM

TECHNICAL FIELD

The present invention relates to a phenolic hydroxyl group-containing resin which has excellent alkali developing properties and makes it possible to exhibit high heat resistance in a cured product obtained therefrom, a production method therefor, a photosensitive composition, a resist material, a coating film, a curable composition and a cured product thereof, and a resist underlayer film.

BACKGROUND ART

The phenolic hydroxyl group-containing resin has been widely used in electrical and electronic fields such as a semiconductor sealing material or a printed circuit board insulating material, as a curable resin composition which has the phenolic hydroxyl group-containing resin per se as the main agent or a curing agent for as an epoxy resin, etc., from the viewpoint of the fact that a cured product obtained therefrom has excellent heat resistance and moisture resistance, in addition to being used for adhesives, molding materials, paint, photoresist materials, epoxy resin raw materials, or curing agents for epoxy resins.

Among these, in the field of semiconductor resist materials, a cresol novolac resin is preferably utilized (refer to PTL 1) since a cured product obtained therefrom exhibits high heat resistance. However, the conventional novolac resin obtained by reaction of cresol with formalin in the presence of an acid catalyst, described in PTL 1 has excellent heat resistance, but does not have sufficient alkali developing properties.

In addition, from the viewpoint of the fact that a compound having a cylindrical structure called a calixarene structure has a high glass transition temperature or a high melting point, and excellent heat stability, applications to various electric and electronic materials are expected. For example, a 1-naphthol type calix [4] arene compound obtained by reacting 1-naphthol and formaldehyde in a proportion in which the molar ratio [1-naphthol/formaldehyde] becomes equal to or less than 1.0 under basic catalyst conditions such as sodium hydroxide is known (refer to PTL 2). However, the 1-naphthol type calix (4) arene compound described in PTL 2 does not have sufficient solubility in general-purpose organic solvents, and thus, applications to adhesives or paints, photoresists, printed circuit boards are difficult.

CITATION LIST

Patent Literature

[PTL 1] JP-A-2013-195497
[PTL 2] JP-A-2012-162474

SUMMARY OF INVENTION

Technical Problem

Therefore, an object of the present invention is to provide a phenolic hydroxyl group-containing resin which has excellent alkali developing properties and makes it possible to exhibit high heat resistance in a cured product obtained therefrom, a production method therefor, a photosensitive composition, a resist material, a coating film, a curable composition and a cured product thereof, and a resist underlayer film.

Solution to Problem

As a result of intensive studies to solve the above problems, the present inventor found that in the case where a calixarene compound formed of an alkyl group- or an aryl group-containing phenol and paraldehyde is used as a resist material, the resin has alkali developing properties, and makes it possible to exhibit high heat resistance in a cured product obtained therefrom, thereby completing the present invention.

That is, the present invention relates to a phenolic hydroxyl group-containing resin which contains a compound (A) having a molecular structure represented by Structural Formula (1).

[Chem. 1]

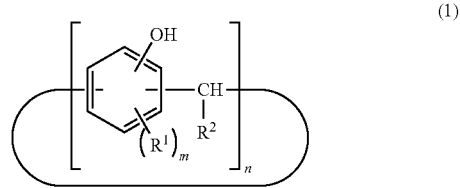

(In the formula, $R^1$ represents an alkyl group, an alkoxy group, or an aryl group, $R^2$ represents a hydrogen atom, an alkyl group, or an aryl group, m is an integer of 1 to 3, and n is an integer of 2 to 15. In the case where m is 2 or more, plural $R^1$'s may be the same as or different from each other.)

The present invention still further relates to a production method for a phenolic hydroxyl group-containing resin, which includes reacting a substituted phenol represented by the following Structural Formula (2) with paraldehyde in the presence of an acid catalyst in an organic solvent.

[Chem. 2]

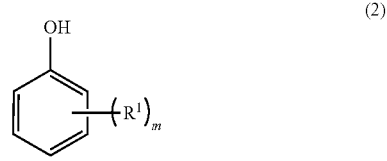

(In the formula, $R^1$ represents an alkyl group, an alkoxy group, or an aryl group, and m is an integer of 1 to 3.)

The present invention further relates to a photosensitive composition containing the phenolic hydroxyl group-containing resin and a photosensitive agent.

The present invention still further relates to a resist composition including the photosensitive composition.

The present invention still further relates to a coating film formed of the photosensitive composition.

The present invention still further relates to a curable composition containing the phenolic hydroxyl group-containing resin and a curing agent.

The present invention still further relates to a cured product obtained by curing the curable composition.

The present invention still further relates to a resist underlayer film obtained by curing the curable composition.

Advantageous Effects of Invention

According to the present invention, it is possible to provide a phenolic hydroxyl group-containing resin which has excellent alkali developing properties and makes it possible to exhibit high heat resistance in a cured product obtained therefrom, a production method therefor, a photosensitive composition, a resist material, and a coating film.

BRIEF DESCRIPTION OF DRAWINGS

FIG. 1 is a GPC chart of a phenolic hydroxyl group-containing resin (1) obtained in Example 1.

FIG. 2 is an MS spectrum of the phenolic hydroxyl group-containing resin (1) obtained in Example 1.

FIG. 3 is a GPC chart of a phenolic hydroxyl group-containing resin (2) obtained in Example 2.

DESCRIPTION OF EMBODIMENTS

The phenolic hydroxyl group-containing resin of the present invention contains the compound (A) having a molecular structure represented by the following Structural Formula (1).

[Chem. 3]

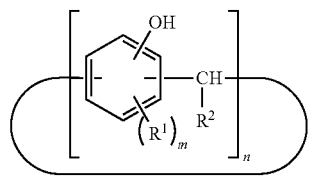

(1)

(In the formula, $R^1$ represents an alkyl group, an alkoxy group, or an aryl group, $R^2$ represents a hydrogen atom, an alkyl group, or an aryl group, m is an integer of 1 to 3, and n is an integer of 2 to 15. In the case where m is 2 or more, plural $R^1$'s may be the same as or different from each other.)

A cresol novolac resin which has been widely used as a resist material in the related art exhibits high heat resistance in a cured product obtained therefrom, but does not have sufficient alkali developing properties. Thus, as a means of improving the alkali developing properties, a method of adjusting the molecular weight of the cresol novolac resin so as to provide a low molecular weight is low is exemplified, but in the above method, the heat resistance of a cured product obtained therefrom is low because of the low molecular weight, and thus, it is difficult to obtain a resin which has excellent alkali developing properties and exhibits high heat resistance in a cured product obtained therefrom.

In contrast, a compound (A) having a molecular structure represented by Structural Formula (1) has a low molecular weight compared with cresol novolac resins in the related art by having a calixarene type cylindrical structure, and makes it possible to exhibit high heat resistance in a cured product obtained therefrom. Accordingly, the phenolic hydroxyl group-containing resin of the present invention containing the compound (A) has excellent alkali developing properties and the cured product obtained therefrom can exhibit high heat resistance.

In addition, a naphthol type calixarene type compound known in the related art has a high glass transition temperature or a high melting point, and excellent heat stability, but does not have sufficient compatibility with general-purpose organic solvents, other resin components, and additives. In contrast, the compound (A) can exhibit high solvent solubility while maintaining high heat resistance which is a characteristic of a calixarene type compound by having a structural portion derived from phenol having an alkyl group, an alkoxy group, or an aryl group, instead of a naphthol structure.

$R^1$ in Structural Formula (1) is an alkyl group, an alkoxy group, or an aryl group, and as the alkyl group, a methyl group, an ethyl group, a propyl group, a butyl group, a pentyl group, a hexyl group, and a cyclohexyl group are exemplified, as the alkoxy group, a methoxy group, an ethoxy group, a propyloxy group, and a butoxy group are exemplified, and as the aryl group, a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group are exemplified. In the case where m in Structural Formula (1) is 2 or more, plural $R^1$'s may be the same as or different from each other. Among them, from the viewpoint of the fact that a phenolic hydroxyl group-containing resin having excellent alkali developing properties is obtained, an alkyl group is preferable, an alkyl group having 1 to 4 carbon atoms such as a methyl group, an ethyl group, a propyl group, or a butyl group is more preferable, and a methyl group is particularly preferable.

The value of m in Structural Formula (1) is an integer of 1 to 3. Among them, from the viewpoint of the fact that a phenolic hydroxyl group-containing resin which has excellent alkali developing properties and exhibits high heat resistance in a cured product thereof is obtained, m is preferably 1.

In the case where the value of m in Structural Formula (1) is 1, the position of an aromatic carbon atom to which the phenolic hydroxyl group in Structural Formula (1) is bonded and an aromatic carbon atom to which the substituent $R^1$ is bonded is preferably a meta position from the viewpoint of excellent reactivity. Accordingly, the phenolic hydroxyl group-containing resin of the present invention represented by Structural Formula (1) preferably contains the compound (A-1) having the molecular structure represented by the following Structural Formula (1-1).

[Chem. 4]

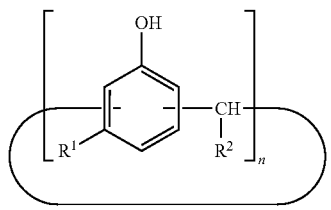

(1-1)

(In the formula, $R^1$ represents an alkyl group or an aryl group, $R^2$ represents a hydrogen atom, an alkyl group, or an aryl group, and n is an integer of 2 to 15.)

$R^2$ in Structural Formula (1) is a hydrogen atom, an alkyl group, or an aryl group, and as the alkyl group, a methyl group, an ethyl group, a propyl group, a butyl group, a pentyl group, a hexyl group, and a cyclohexyl group are exemplified, and as the aryl group, a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group are exemplified. Among them, from the viewpoint of the fact that a phenolic hydroxyl group-containing resin which has excellent alkali developing properties and exhibits high heat resistance in a cured product obtained therefrom is obtained, an alkyl group is preferable, and a methyl group is more preferable.

Specifically, the phenolic hydroxyl group-containing resin of the present invention can be produced by a method of reacting a substituted phenol represented by the following Structural Formula (2) with paraldehyde in the presence of an acid catalyst in an organic solvent.

[Chem. 5]

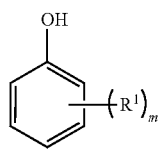

(2)

(In the formula, $R^1$ represents an alkyl group, an alkoxy group, or an aryl group, and m is an integer of 1 to 3.)

That is, in the production method of the present invention, the substituted phenol represented by Structural Formula (2) as a substituted phenol and paraldehyde which is a cyclic trimer of acetaldehyde as an aldehyde compound are reacted in the presence of an acid catalyst in an organic solvent, and as a result, the calixarene type phenolic hydroxyl group-containing resin can be efficiently produced.

The substituted phenol used in the production method of the present invention is a compound represented by the following Structural Formula (2), and $R^1$ in the formula is an alkyl group, an alkoxy group, or an aryl group.

[Chem. 6]

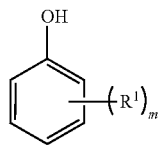

(2)

(In the formula, $R^1$ represents an alkyl group, an alkoxy group, or an aryl group, and m is an integer of 1 to 3.)

Specific examples thereof include alkyl groups such as a methyl group, an ethyl group, a propyl group, a butyl group, a pentyl group, a hexyl group, and a cyclohexyl group; alkoxy groups such as a methoxy group, an ethoxy group, a propyloxy group, and a butoxy group, and aryl groups such as a phenyl group, a hydroxyphenyl group, a dihydroxyphenyl group, a hydroxyalkoxyphenyl group, an alkoxyphenyl group, a tolyl group, a xylyl group, a naphthyl group, a hydroxynaphthyl group, and a dihydroxynaphthyl group.

Specific examples of such a substituted phenol include alkyl-substituted phenols such as cresol, xylenol, trimethyl phenol, ethyl phenol, propyl phenol, and butyl phenol; alkoxy-substituted phenols such as methoxyphenol, ethoxyphenol, propoxyphenol, and butoxyphenol; and aryl-substituted phenols such as phenyl phenol and naphthyl phenol. The substituted phenol represented by Structural Formula (2) may be used alone respectively, or in combination of two or more types thereof.

Among these, from the viewpoint of the fact that a phenolic hydroxyl group-containing resin having excellent alkali developing properties is obtained, $R^1$ is preferably an alkyl group, more preferably an alkyl group having 1 to 4 carbon atoms such as a methyl group, an ethyl group, a propyl group, or a butyl group, and particularly preferably a methyl group.

In addition, the value of m in Structural Formula (2) is an integer of 1 to 3. Among these, from the viewpoint of the fact that a phenolic hydroxyl group-containing resin which has excellent alkali developing properties and exhibits high heat resistance in a cured product obtained therefrom is obtained, m is preferably 1.

Therefore, the substituted phenol represented by Structural Formula (2) is preferably cresol in which $R^1$ is a methyl group and m is 1, and from the viewpoint of excellent reactivity, meta-cresol is particularly preferable.

In the production method of the present invention, paraldehyde which is a cyclic trimer of acetaldehyde or metaldehyde which is a cyclic tetramer is used as the aldehyde compound described above. As the reaction proportion between the substituted phenol and acetaldehyde, acetaldehyde is preferably within a range of 0.6 to 1.5 moles with respect to 1 mole of the substituted phenol, from the viewpoint of the fact that the calixarene type phenolic hydroxyl group-containing resin represented by Structural Formula (1) is efficiently produced.

Examples of the organic solvent used in the present invention include esters such as ethyl acetate, methyl acetate, butyl acetate, methyl lactate, ethyl lactate, and butyl lactate, ketones such as acetone, methyl ethyl ketone, methyl isobutyl ketone, diacetone alcohol, and cyclohexane, alcohols such as methanol, ethanol, n-propanol, isopropanol, n-butanol, isobutanol, t-butanol, and ethyl hexanol, ethers such as dimethyl ether, diethyl ether, isopropyl ether, methyl cellosolve, cellosolve, butyl cellosolve, THF, dioxane, and butyl carbitol, and alcohol ethers such as methoxyethanol, ethoxyethanol, and butoxyethanol. These may be used alone respectively, or in combination of two or more types thereof. Among the above organic solvents, from the viewpoint of the fact that a phenolic hydroxyl group-containing resin which has excellent alkali developing properties and exhibits high heat resistance in a cured product obtained therefrom is obtained, as the organic solvent, alcohols or alcohol ethers are preferably used.

The amount of organic solvent used is preferably within a range of 100 to 400 parts by mass with respect to the total 100 parts by mass of the substituted phenol and paraldehyde from the viewpoint of the fact that the phenolic hydroxyl group-containing resin of the present invention is efficiently generated.

Examples of the acid catalyst used in the production method of the present invention include inorganic acids such as hydrochloric acid, sulfuric acid, and phosphoric acid, organic acids such as methanesulfonic acid, para-toluenesulfonic acid, and oxalic acid, or Lewis acids such as boron trifluoride, anhydrous aluminum chloride, and zinc chloride.

These may be used alone respectively, or in combination of two or more types thereof. Among these, an organic acid is preferable from the viewpoint of the fact that the phenolic hydroxyl group-containing resin of the present invention having high catalytic activity is efficiently generated. In addition, the amount of acid catalyst used is preferably within a range of 1 to 100 parts by mass with respect to the total 100 parts by mass of the substituted phenol and paraldehyde from the viewpoint of the fact that sufficient catalytic activity is obtained.

The reaction of the substituted phenol with paraldehyde, for example, is performed by reacting the substituted phenol with paraldehyde for about 8 to 15 hours under the temperature condition of 80° C. to 120° C. After the reaction ends, an organic solvent which is a good solvent for the generated phenolic hydroxyl group-containing resin was added to the reaction system, then, liquid-liquid separation washing was performed with water, and the organic solvent used is distilled off by heating under reduced pressure, whereby a phenolic hydroxyl group-containing resin of the present invention can be obtained.

The weight average molecular weight (Mw) of the phenolic hydroxyl group-containing resin of the present invention obtained in this manner is preferably within a range of 1,000 to 25,000 from the viewpoint of the fact that alkali developing properties are excellent and it is possible to exhibit high heat resistance in an obtained cured product. Among these, in the case of being used in a general resist film, the weight average molecular weight is preferably within a range of 1,000 to 10,000, and in the case of being used in applications where higher heat resistance of an underlayer film or the like is required, the weight average molecular weight is preferably within a range of 8,000 to 25,000.

In addition, the phenolic hydroxyl group-containing resin of the present invention preferably has a structure in which the value of n in Structural Formula (1) is 4 at 5% to 50% or more from the viewpoint of excellent balance between developing properties and heat resistance.

The weight average molecular weight (Mw) of the phenolic hydroxyl group-containing resin in the present invention is a value measured by GPC under the following conditions. In addition, the content of each component of the phenolic hydroxyl group-containing resin is a value calculated from the area ratio of the GPC chart measured under the following conditions.

<Measurement Conditions of GPC>

Measuring apparatus: "HLC-8220 GPC" manufactured by Tosoh Corporation,

Column: Guard Column "HHR-H" (6.0 mmI.D.×4 cm) manufactured by Tosoh Corporation "TSK-GEL GMHHR-N" (7.8 mmI.D.×30 cm) manufactured by Tosoh Corporation "TSK-GEL GMHHR-N" (7.8 mmI.D.×30 cm) manufactured by Tosoh Corporation "TSK-GEL GMHHR-N" (7.8 mmI.D.×30 cm) manufactured by Tosoh Corporation "TSK-GEL GMHHR-N" (7.8 mmI.D.×30 cm) manufactured by Tosoh Corporation Detector: ELSD ("ELSD2000" manufactured by Alltech Japan Co., Ltd.), Data processing: "GPC-8020 model II data analysis version 4.30" manufactured by Tosoh Corporation Measurement conditions: column temperature 40° C.
eluent tetrahydrofuran (THF)
flow rate 1.0 ml/min Sample: a solution (5 μl) obtained by filtering a tetrahydrofuran solution of 1.0% by mass in terms of the resin solid content through a microfilter.

Standard sample: according to the measurement manual of the "GPC-8020 model II data analysis version 4.30", the following monodisperse polystyrene of which the molecular weight is known was used.

(Monodisperse Polystyrene)

"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
"F-288" manufactured by Tosoh Corporation
"F-550" manufactured by Tosoh Corporation In addition, the content of the substituted phenol remaining in the phenolic hydroxyl group-containing resin of the present invention is preferably less than 0.5% from the viewpoint of the fact that high heat resistance is exhibited in a cured product obtained therefrom. The content of the substituted phenol remaining in the phenolic hydroxyl group-containing resin in the present invention is a value calculated from the GPC chart measured in the conditions described above, and is a ratio of the peak area derived from the substituted phenol to the peak area of the entire phenolic hydroxyl group-containing resin.

The photosensitive composition of the present invention contains the phenolic hydroxyl group-containing resin and a photosensitive agent as essential components.

As the photosensitive agent used in the present invention, a compound having a quinonediazide group is exemplified. Specific examples of the compound having a quinonediazide group include a complete ester compound of an aromatic (poly)hydroxyl compound and sulfonic acid having a quinonediazide group such as naphthoquinone-1,2-diazido-5-sulfonic acid, naphthoquinone-1,2-diazido-4-sulfonic acid, or ortho-anthraquinonediazidosulfonic acid, a partial ester compound, an amidated product, and a partially amidated product.

Examples of the aromatic (poly)hydroxyl compound used here include polyhydroxybenzophenone compounds such as 2,3,4-trihydroxybenzophenone, 2,4,4'-trihydroxybenzophenone, 2,4,6-trihydroxybenzophenone, 2,3,6-trihydroxybenzophenone, 2,3,4-trihydroxy-2'-methylbenzophenone, 2,3,4,4'-tetrahydroxybenzophenone, 2,2',4,4'-tetrahydroxybenzophenone, 2,3',4,4',6-pentahydroxybenzophenone, 2,2',3,4,4'-pentahydroxybenzophenone, 2,2',3,4,5-pentahydroxybenzophenone, 2,3',4,4',5',6-hexahydroxybenzophenone, and 2,3,3',4,4',5'-hexahydroxybenzophenone;

bis[(poly)hydroxyphenyl]alkane compounds such as bis (2,4-dihydroxyphenyl)methane, bis(2,3,4-trihydroxyphenyl)methane, 2-(4-hydroxyphenyl)-2-(4'-hydroxyphenyl) propane, 2-(2,4-dihydroxyphenyl)-2-(2',4'-dihydroxyphenyl)propane, 2-(2,3,4-trihydroxyphenyl)-2-(2',3',4'-trihydroxyphenyl)propane, 4,4'-{1-[4-[2-(4-hydroxyphenyl)-2-propyl]phenyl]ethylidene}bisphenol, and 3,3'-dimethyl-{1-[4-[2-(3-methyl-4-hydroxyphenyl)-2-propyl]phenyl]ethylidene}bisphenol;

tris(hydroxyphenyl)methane compounds such as tris(4-hydroxyphenyl)methane, bis(4-hydroxy-3,5-dimethylphenyl)-4-hydroxyphenyl methane, bis(4-hydroxy-2,5-dimethylphenyl)-4-hydroxyphenyl methane, bis(4-hydroxy-3,5-dimethylphenyl)-2-hydroxyphenyl methane, bis(4-hydroxy-2,5-dimethylphenyl)-2-hydroxyphenyl methane, bis(4-hydroxy-2,5-dimethylphenyl)-3,4-dihydroxyphenyl methane, and bis(4-hydroxy-3,5-dimethylphenyl)-3,4-dihydroxyphenyl methane, and methyl-substituted products thereof;

bis(cyclohexyl-hydroxyphenyl)(hydroxyphenyl)methane compounds such as bis(3-cyclohexyl-4-hydroxyphenyl)-3-hydroxyphenyl methane, bis(3-cyclohexyl-4-hydroxyphenyl)-2-hydroxyphenyl methane, bis(3-cyclohexyl-4-hydroxyphenyl)-4-hydroxyphenyl methane, bis(5-cyclohexyl-4-hydroxy-2-methylphenyl)-2-hydroxyphenyl methane, bis(5-cyclohexyl-4-hydroxy-2-methylphenyl)-3-hydroxyphenyl methane, bis(5-cyclohexyl-4-hydroxy-2-methylphenyl)-4-hydroxyphenyl methane, bis(3-cyclohexyl-2-hydroxyphenyl)-3-hydroxyphenyl methane, bis(5-cyclohexyl-4-hydroxy-3-methylphenyl)-4-hydroxyphenyl methane, bis(5-cyclohexyl-4-hydroxy-3-methylphenyl)-3-hydroxyphenyl methane, bis(5-cyclohexyl-4-hydroxy-3-methylphenyl)-2-hydroxyphenyl methane, bis(3-cyclohexyl-2-hydroxyphenyl)-4-hydroxyphenyl methane, bis(3-cyclohexyl-2-hydroxyphenyl)-2-hydroxyphenyl methane, bis(5-cyclohexyl-2-hydroxy-4-methylphenyl)-2-hydroxyphenyl methane, and bis(5-cyclohexyl-2-hydroxy-4-methylphenyl)-4-hydroxyphenyl methane, and methyl-substituted products thereof. These photosensitive agents may be used alone respectively, or in combination of two or more types thereof.

The blending amount of photosensitive agent in the photosensitive composition of the present invention is preferably in a proportion within a range of 5 to 50 parts by mass with respect to 100 parts by mass of the phenolic hydroxyl group-containing resin from the viewpoint of the fact that a composition having excellent photosensitivity is obtained.

In the photosensitive composition of the present invention, in addition to the phenolic hydroxyl group-containing resin, other resins may be used in combination. As other resins, any resin can be used as long as the resin is soluble in an alkali developer, or the resin is dissolved in an alkali developer by using in combination with an additive such as an acid generator.

Example of other resin used here include (x1) phenolic resins other than the phenolic hydroxyl group-containing resin, (x2) a homopolymer or a copolymer of a styrene compound containing a hydroxyl group such as p-hydroxystyrene and p-(1,1,1,3,3,3-hexafluoro-2-hydroxypropyl) styrene, (x3) those obtained by modifying the hydroxyl group of the (x1) or the (x2) with an acid-decomposable group such as a t-butoxycarbonyl group or a benzyloxycarbonyl group, (x4) a homopolymer or a copolymer of (meth)acrylic acid, and (x5) an alternating copolymer of alicyclic polymerizable monomer such as a norbornene compound or a tetracyclododecene compound and maleic anhydride or maleimide.

Examples of other phenolic resins (x1) include phenolic resins such as a phenol novolac resin, a cresol novolac resin, a naphthol novolac resin, a co-condensed novolac resin using various phenolic compounds, an aromatic hydrocarbon formaldehyde resin-modified phenolic resin, a dicyclopentadiene phenol adduct type resin, a phenol aralkyl resin (xylok resin), a naphthol aralkyl resin, a trimethylol methane resin, a tetraphenylol ethane resin, a biphenyl-modified phenolic resin (polyphenol compound in which a phenolic nucleus is linked by a bismethylene group), a biphenyl-modified naphthol resin (polynaphthol compound in which a phenolic nucleus is linked by a bismethylene group), an aminotriazine-modified phenolic resin (polyphenol compound in which a phenolic nucleus is linked by melamine, benzoguanamine, or the like), and an aromatic ring-modified novolac resin containing an alkoxy group (polyphenol compound in which a phenolic nucleus and an aromatic ring containing an alkoxy group are linked by formaldehyde).

Among the other resins (x1), a co-condensation novolac resin of a cresol novolac resin or cresol and other phenolic compounds is preferable from the viewpoint of the fact that a photosensitive resin composition which has high sensitivity and makes it possible to exhibit high heat resistance in a cured product obtained therefrom is obtained. A cresol novolac resin or a co-condensation novolac resin of cresol and other phenolic compounds is, specifically, a novolac resin obtained by using at least one cresol selected from the group consisting of o-cresol, m-cresol, and p-cresol and an aldehyde compound as essential raw materials and suitably using other compounds containing a phenolic hydroxyl group in combination.

Examples of the compounds containing a phenolic hydroxyl group other than the cresols include phenol; xylenols such as 2,3-xylenol, 2,4-xylenol, 2,5-xylenol, 2,6-xylenol, 3,4-xylenol, and 3,5-xylenol; ethylphenols such as o-ethylphenol, m-ethylphenol, and p-ethylphenol; butylphenols such as isopropylphenol, butylphenol, and p-t-butylphenol; alkylphenols such as p-pentylphenol, p-octylphenol, p-nonylphenol, and p-cumylphenol; halogenated phenols such as fluorophenol, chlorophenol, bromophenol, and iodophenol; monosubstituted phenols such as p-phenylphenol, aminophenol, nitrophenol, dinitrophenol, and trinitrophenol; condensed polycyclic phenols such as 1-naphthol and 2-naphthol; and polyphenols such as resorcinol, alkyl resorcinol, pyrogallol, catechol, alkyl catechol, hydroquinone, alkyl hydroquinone, phloroglucinol, bisphenol A, bisphenol F, bisphenol S, and dihydroxynaphthalene. These other compounds containing a phenolic hydroxyl group may be used alone respectively, or in combination of two or more types thereof. In the case of using these other compounds containing a phenolic hydroxyl group, as the amount used, these other phenolic compounds is preferably a proportion within a range of 0.05 to 1 mole with respect to the total 1 mole of the cresol raw materials.

In addition, examples of the aldehyde compound include formaldehyde, para-formaldehyde, trioxane, acetaldehyde, propionaldehyde, polyoxymethylene, chloral, hexamethylenetetramine, furfural, glyoxal, n-butyraldehyde, caproaldehyde, allyl aldehyde, benzaldehyde, crotonaldehyde, acrolein, tetraoxymethylene, phenyl acetaldehyde, o-tolualdehyde, and salicylaldehyde, and these may be used alone respectively, or in combination of two or more types thereof. Among these, formaldehyde is preferable, and formaldehyde and other aldehyde compounds may be used in combination. In the case where formaldehyde and other aldehyde compounds are used in combination, the amount of other aldehyde compounds used is preferably within a range of 0.05 to 1 mole with respect to 1 mole of formaldehyde.

As the proportion of a reaction of a phenolic hydroxyl group-containing compound with an aldehyde compound at the time of producing a novolac resin, the aldehyde compound with respect to 1 mole of the phenolic compound is preferably within a range of 0.3 to 1.6 mole, and more preferably within a range of 0.5 to 1.3 from the viewpoint of the fact that a photosensitive resin composition which has high sensitivity and exhibits high heat resistance in a cured product obtained therefrom is obtained.

The reaction of the compound containing a phenolic hydroxyl group with the aldehyde compound is performed under the temperature condition of 60° C. to 140° C. in the presence of an acid catalyst, and next, a method of removing water and the residual monomer under reduced pressure conditions is exemplified. Examples of the acid catalyst used here include oxalic acid, sulfuric acid, hydrochloric acid, phenol sulfonic acid, p-toluenesulfonic acid, zinc acetate, and manganese acetate, and these may be used alone respectively, or in combination of two or more types thereof. Among these, from the viewpoint of excellent catalytic activity, oxalic acid is preferable.

Among the cresol novolac resin or a co-condensation novolac resin of cresol and other phenolic compounds described above in detail, a cresol novolac resin obtained by using meta-cresol alone or a cresol novolac resin obtained by using meta-cresol and para-cresol in combination is preferable. In addition, the reaction molar ratio [meta-cresol/para-cresol] of meta-cresol to para-cresol in the latter is preferably within a range of 9/1 to 2/8, and more preferably within a range of 7/3 to 2/8 since a photosensitive resin composition excellent in balance between sensitivity and heat resistance in the cured product is obtained.

In the case where other resins are used, the blending proportion of the phenolic hydroxyl group-containing resin of the present invention to other resins can be arbitrarily adjusted depending on the desired application. For example, from the viewpoint of the fact that the phenolic hydroxyl group-containing resin of the present invention has excellent photosensitivity when combined with a photosensitive agent, excellent resolution, and excellent heat resistance in a cured product, a photosensitive composition having the phenolic hydroxyl group-containing resin as a main component is optimal to resist applications. At this time, the ratio (proportion) of the phenolic hydroxyl group-containing resin in the total resin components is preferably equal to or greater than 60% by mass, and more preferably equal to or greater than 80% by mass from the viewpoint of the fact that a curable composition having high photosensitivity, excellent resolution, and excellent heat resistance in a cured product is obtained.

In addition, by taking advantage of the characteristic that the photosensitivity of the phenolic hydroxyl group-containing resin is excellent, this resin can be used as a sensitivity improver. In this case, as the blending proportion between the phenolic hydroxyl group-containing resin and other resins, the phenolic hydroxyl group-containing resin is preferably within a range of 3 to 80 parts by mass with respect to 100 parts by mass of other resins.

In the case where other resins are used, the blending amount of photosensitive agent in the photosensitive composition of the present invention is preferably in a proportion within a range of 5 to 50 parts by mass with respect to the total 100 parts by mass of the resin components in the composition from the viewpoint of the fact that a photosensitive composition having excellent photosensitivity is obtained.

The photosensitive composition of the present invention may contain a surfactant for the purpose of improving the film forming properties or the adhesion of patterns in the case of being used in resist applications, and reducing development defects. Examples of the surfactant used here include nonionic surfactants such as polyoxyethylene alkyl ether compounds including polyoxyethylene lauryl ether, polyoxyethylene stearyl ether, polyoxyethylene cetyl ether, and polyoxyethylene oleyl ether, polyoxyethylene alkyl allyl ether compounds including polyoxyethylene octylphenol ether and polyoxyethylene nonylphenol ether, sorbitan fatty acid ester compounds including a polyoxyethylene-polyoxypropylene block copolymer, sorbitan monolaurate, sorbitan monopalmitate, sorbitan monostearate, sorbitan monooleate, sorbitan trioleate, and sorbitan tristearate, and polyoxyethylene sorbitan fatty acid ester compounds including polyoxyethylene sorbitan monolaurate, polyoxyethylene sorbitan monopalmitate, polyoxyethylene sorbitan monostearate, polyoxyethylene sorbitan trioleate, and polyoxyethylene sorbitan tristearate; fluorine-based surfactants having a fluorine atom in the molecular structure such as a copolymer of a polymerizable monomer having a fluoroaliphatic group and [poly(oxyalkylene)](meth)acrylate; and silicone surfactants having a silicone structural portion in the molecular structure. These may be used alone respectively, or in combination of two or more types thereof.

The blending amount of these surfactants is preferably within a range of 0.001 to 2 parts by mass with respect to 100 parts by mass of the resin solid content in the curable composition of the present invention.

In the case where the photosensitive composition of the present invention is used in photoresist applications, the phenolic hydroxyl group-containing resin and the photosensitive agent, and if necessary, various additives such as other resins, a surfactant, a dye, a filler, a crosslinking agent, and a dissolution accelerator, are added and dissolved in an organic solvent to there by obtain a resist composition. The resist composition may be directly used as a positive type resist solution, or that obtained by applying the resist composition into a film shape and removing the solvent may be used as a positive type resist film. As the support film when used as a resist film, synthetic resin films such as polyethylene, polypropylene, polycarbonate, and polyethylene terephthalate can be exemplified, and the support film may be a single layer film or a plurality of laminated film. In addition, the surface of the support film may be a surface subjected to a corona treatment or applied with a release agent.

The organic solvent used in the resist composition of the present invention is not particularly limited, and examples thereof include alkylene glycol monoalkyl ethers such as ethylene glycol monomethyl ether, ethylene glycol monoethyl ether, ethylene glycol monopropyl ether, ethylene glycol monobutyl ether, and propylene glycol monomethyl ether; dialkylene glycol dialkyl ethers such as diethylene glycol dimethyl ether, diethylene glycol diethyl ether, diethylene glycol dipropyl ether, and diethylene glycol dibutyl ether; akylene glycol alkyl ether acetates such as ethylene glycol monomethyl ether acetate, ethylene glycol monoethyl ether acetate, and propylene glycol monomethyl ether acetate; ketone compounds such as acetone, methyl ethyl ketone, cyclohexanone, and methyl amyl ketone; cyclic ethers such as dioxane; and ester compounds such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate, and these may be used alone respectively, or in combination of two or more types thereof.

The resist composition of the present invention can be prepared by blending the above-described respective components and mixing these using a stirrer or the like. In addition, in the case where the resin composition for photoresist contains a filler or a pigment, it is possible to prepare the composition by dispersing or mixing using a dispersing device such as a dissolver, a homogenizer, or a three-roll mill.

In the method of photolithography using the resist composition of the present invention, for example, the resist composition is applied onto an object on which silicon substrate photolithography is performed, and prebaked under a temperature condition of 60° C. to 150° C. The coating method at this time may be any method of spin coating, roll coating, flow coating, dip coating, spray coating, and doctor blade coating. Next, a resist pattern is prepared, from the viewpoint of the fact that the resist composition of the present invention is a positive type, by exposing the target resist pattern through a predetermined mask and by dissolving the exposed portions in an alkali developer, a resist pattern is formed. A resist pattern having excellent resolution can be formed of the resist composition of the present invention since both alkali solubility of the exposed portion and resistance to alkali solubility of the unexposed portion are high.

The curable composition of the present invention contains the phenolic hydroxyl group-containing resin and a curing agent as essential components. In the curable composition of the present invention, in addition to the phenolic hydroxyl group-containing resin of the present invention, other resins (y) may be used in combination. Examples of other resins (y) used here include various novolac resins, an addition polymerization resin of an alicyclic diene compound such as dicyclopentadiene and a phenol compound, a modified novolac resin of a phenolic hydroxyl group-containing compound and an alkoxy group-containing aromatic compound, a phenol aralkyl resin (xylok resin), a naphthol aralkyl resin, a trimethylol methane resin, a tetraphenylol ethane resin, a biphenyl-modified phenolic resin, a biphenyl-modified naphthol resin, an aminotriazine-modified phenolic resin, a naphthylene ether resin, and various vinyl polymers.

More specific examples of the various novolac resin include alkylphenols such as phenol, cresol, and xylenol, bisphenols such as phenylphenol, resorcinol, biphenyl, bisphenol A, and bisphenol F, and a polymer obtained by reacting a compound containing a phenolic hydroxyl group such as naphthol or dihydroxynaphthalene with an aldehyde compound under acid catalyst conditions.

Examples of the various vinyl polymers include homopolymers or copolymers of vinyl compounds such as polyhydroxystyrene, polystyrene, polyvinyl naphthalene, polyvinyl anthracene, polyvinyl carbazole, polyindene, polyacenaphthylene, polynorbornene, polycyclodecene, polytetracyclododecene, polynortricyclene, and poly(meth)acrylate.

In the case where other resins are used, the blending proportion of the phenolic hydroxyl group-containing resin of the present invention to other resins (Y) can be arbitrarily set depending on the application, and the blending proportion is preferably in a proportion in which other resins (y) become 0.5 to 100 parts by mass with respect to 100 parts by mass of the phenolic hydroxyl group-containing resin of the present invention from the viewpoint of the fact that excellent effects are more significantly expressed in the dry etching resistance and the resistance to thermal decomposition achieved by the present invention.

Examples of the curing agent used in the present invention include a melamine compound substituted with at least one group selected from a methylol group, an alkoxymethyl group, and an acyloxymethyl group, a guanamine compound, a glycoluril compound, a urea compound, a resole resin, an epoxy compound, an isocyanate compound, an azide compound, a compound including a double bond such as an alkenyl ether group, acid anhydride, and an oxazoline compound.

Examples of the melamine compound include hexamethylolmelamine, hexamethoxymethylmelamine, a compound in which 1 to 6 methylol groups in hexamethylolmelamine have been methoxymethylated, hexamethoxyethylmelamine, hexaacyloxymethylmelamine, and a compound in which 1 to 6 methylol groups in hexamethylolmelamine have been acyloxymethylated.

Examples of the guanamine compound include tetramethylolguanamine, tetramethoxymethylguanamine, tetramethoxymethylbenzoguanamine, a compound in which 1 to 4 methylol groups in tetramethylolguanamine have been methoxymethylated, tetramethoxyethylguanamine, tetraacyloxyguanamine, and a compound in which 1 to 4 methylol groups in tetramethylolguanamine have been acyloxymethylated.

Examples of the glycoluril compound include 1,3,4,6-tetrakis(methoxymethyl) glycoluril, 1,3,4,6-tetrakis(butoxymethyl) glycoluril, and 1,3,4,6-tetrakis(hydroxymethyl) glycoluril.

Examples of the urea compound include 1,3-bis(hydroxymethyl)urea, 1,1,3,3-tetrakis(butoxymethyl)urea, and 1,1,3,3-tetrakis(methoxymethyl)urea.

Examples of the resole resin include alkylphenols such as phenol, cresol, and xylenol, bisphenols such as phenylphenol, resorcinol, biphenyl, bisphenol A, and bisphenol F, and a polymer obtained by reacting a compound containing a phenolic hydroxyl group such as naphthol or dihydroxynaphthalene with an aldehyde compound under alkali catalyst conditions.

Examples of the epoxy compound include tris(2,3-epoxypropyl)isocyanurate, trimethylol methane triglycidyl ether, trimethylol propane triglycidyl ether, triethylol ethane triglycidyl ether, glycidyl ether of a dihydroxynaphthalene derivative, glycidyl ether of an addition polymerization resin of an alicyclic diene compound such as dicyclopentadiene and a phenol compound, glycidyl ether of a modified novolac resin of a phenolic hydroxyl group-containing compound and an alkoxy group-containing aromatic compound, and glycidyl ether of a naphthylene ether resin.

Examples of the isocyanurate compound include tolylene diisocyanate, diphenylmethane diisocyanate, hexamethylene diisocyanate, and cyclohexane diisocyanate.

Examples of the azide compound include 1,1'-biphenyl-4,4'-bisazide, 4,4'-methylidenebisazide, and 4,4'-oxybisazide.

Examples of the compound including a double bond such as an alkenyl ether group include ethyleneglycol divinyl ether, triethyleneglycol divinyl ether, 1,2-propanediol divinyl ether, 1,4-butanediol divinyl ether, tetramethyleneglycol divinyl ether, neopentylglycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylolpropane trivinyl ether.

Examples of the acid anhydride include aromatic acid anhydrides such as phthalic anhydride, trimellitic anhydride, pyromellitic anhydride, 3,3',4,4'-benzophenonetetracarboxylic dianhydride, biphenyltetracarboxylic dianhydride, 4,4'-(isopropylidene)diphthalic anhydride, and 4,4'-(hexafluoro isopropylidene)diphthalic anhydride; and alicyclic carboxylic acid anhydrides such as tetrahydrophthalic anhydride, methyltetrahydrophthalic anhydride, hexahydrophthalic anhydride, methylhexahydrophthalic anhydride, endomethylene tetrahydrophthalic anhydride, dodecenylsuccinic anhydride, and trialkyltetrahydrophthalic anhydride.

Among these, from the viewpoint of the fact that a curable composition having excellent curability and heat resistance in the cured product is obtained, a glycoluril compound, a urea compound, or a resole resin is preferable, and a glycoluril compound is particularly preferable.

The blending amount of the curing agent in the curable composition of the present invention is preferably in a proportion within a range of 0.5 to 50 parts by mass with respect to the total 100 parts by mass of the phenolic hydroxyl group-containing resin of the present invention and other resin (y)s from the viewpoint of the fact that a composition having excellent curability is obtained.

In the case where the curable composition of the present invention is used in resist underlayer film (BARC film) applications, by adding the phenolic hydroxyl group-containing resin of the present invention and the curing agent, and if necessary, various additives such as other resins (y), a surfactant, a dye, a filler, a crosslinking agent, and a dissolution accelerator, and by dissolving them in an organic solvent, a composition for resist underlayer films can be obtained.

The organic solvent used in the composition for resist underlayer films is not particularly limited, and examples thereof include alkylene glycol monoalkyl ethers such as ethylene glycol monomethyl ether, ethylene glycol monoethyl ether, ethylene glycol monopropyl ether, ethylene glycol monobutyl ether, and propylene glycol monomethyl ether; dialkylene glycol dialkyl ethers such as diethylene glycol dimethyl ether, diethylene glycol diethyl ether, diethylene glycol dipropyl ether, and diethylene glycol dibutyl ether; akylene glycol alkyl ether acetates such as ethylene glycol monomethyl ether acetate, ethylene glycol monoethyl ether acetate, and propylene glycol monomethyl ether acetate; ketone compounds such as acetone, methyl ethyl ketone, cyclohexanone, and methyl amyl ketone; cyclic ethers such as dioxane; and ester compounds such as methyl 2-hydroxypropionate, ethyl 2-hydroxypropionate, ethyl 2-hydroxy-2-methylpropionate, ethyl ethoxyacetate, ethyl oxyacetate, methyl 2-hydroxy-3-methylbutanoate, 3-methoxybutyl acetate, 3-methyl-3-methoxybutyl acetate, ethyl formate, ethyl acetate, butyl acetate, methyl acetoacetate, and ethyl acetoacetate, and these may be used alone respectively, or in combination of two or more types thereof.

The composition for resist underlayer films can be prepared by blending the above-described respective components and mixing these using a stirrer or the like. In addition, in the case where the composition for resist underlayer films contains a filler or a pigment, it is possible to prepare the composition by dispersing or mixing using a dispersing device such as a dissolver, a homogenizer, or a three-roll mill.

To prepare a resist underlayer film from the composition for resist underlayer films, for example, a resist underlayer film is formed by a method in which the composition for resist underlayer films is applied onto an object on which photolithography is to be performed such as a silicon substrate, dried under the temperature condition of 100° C. to 200° C., and further cured by heat under the temperature condition of 250° C. to 400° C. Next, a resist pattern is formed on the underlayer film by performing a typical photolithography operation, and a dry etching treatment is performed with a halogen-based plasma gas or the like, thereby forming a resist pattern according to a multilayer resist method.

In the case where the curable composition of the present invention is used in resist permanent film applications, a composition for resist permanent films can be obtained by adding the phenolic hydroxyl group-containing resin of the present invention and the curing agent, and if necessary, various additives such as other resins (y), a surfactant, a dye, a filler, a crosslinking agent, and a dissolution accelerator, to dissolve them in an organic solvent. Examples of the organic solvent as used herein include the same as the organic solvent used in the composition for resist underlayer films.

In the method of photolithography using the composition for resist permanent films, for example, resin components and additive components are dissolved or dispersed in an organic solvent, applied onto an object on which photolithography is performed, such as silicon substrate, and prebaked under a temperature condition of 60° C. to 150° C. The coating method at this time may be any method of spin coating, roll coating, flow coating, dip coating, spray coating, and doctor blade coating. Next, a resist pattern is prepared, but in the case where the composition for resist permanent films is a positive type, a resist pattern is formed by exposing the target resist pattern through a predetermined mask and dissolving the exposed portions in an alkali developer.

The permanent films formed of the composition for resist permanent films can be suitably used, for example, for a solder resist, a packaging material, an underfill material, an adhesive layer for a package such as a circuit element, or an adhesive layer between an integrated circuit element and a circuit board, in the semiconductor devices, and a thin film transistor protective film, a liquid crystal color filter protective film, a black matrix, and a spacer, in the thin displays represented by LCD and OELD.

EXAMPLES

Hereinafter, the present invention will be more specifically described using examples and comparative examples, and "parts" and "%" are based on mass unless otherwise specifically indicated.

In examples and comparative examples of the present invention, GPC was measured under the following conditions.

<Measurement Conditions of GPC>

Measuring apparatus: "HLC-8220 GPC" manufactured by Tosoh Corporation,

Column: Guard Column "HHR-H" (6.0 mmI.D.×4 cm) manufactured by Tosoh Corporation "TSK-GEL GMHHR-N" (7.8 mmI.D.×30 cm) manufactured by Tosoh Corporation "TSK-GEL GMHHR-N" (7.8 mmI.D.×30 cm) manufactured by Tosoh Corporation "TSK-GEL GMHHR-N" (7.8 mmI.D.×30 cm) manufactured by Tosoh Corporation "TSK-GEL GMHHR-N" (7.8 mmI.D.×30 cm) manufactured by Tosoh Corporation "TSK-GEL GMHHR-N" (7.8 mmI.D.×30 cm) manufactured by Tosoh Corporation Detector: ELSD ("ELSD2000" manufactured by Alltech Japan Co., Ltd.), Data processing: "GPC-8020 model II data analysis version 4.30" manufactured by Tosoh Corporation Measurement conditions: column temperature 40° C.

eluent tetrahydrofuran (THF)

flow rate 1.0 ml/min

Sample: a solution (5 µl) obtained by filtering a tetrahydrofuran solution of 1.0% by mass in terms of the resin solid content through a microfilter.

Standard sample: according to the measurement manual of the "GPC-8020 model II data analysis version 4.30", the following monodisperse polystyrene of which the molecular weight is known was used.

(Monodisperse Polystyrene)
"A-500" manufactured by Tosoh Corporation
"A-1000" manufactured by Tosoh Corporation
"A-2500" manufactured by Tosoh Corporation
"A-5000" manufactured by Tosoh Corporation
"F-1" manufactured by Tosoh Corporation
"F-2" manufactured by Tosoh Corporation
"F-4" manufactured by Tosoh Corporation
"F-10" manufactured by Tosoh Corporation
"F-20" manufactured by Tosoh Corporation
"F-40" manufactured by Tosoh Corporation
"F-80" manufactured by Tosoh Corporation
"F-128" manufactured by Tosoh Corporation
"F-288" manufactured by Tosoh Corporation
"F-550" manufactured by Tosoh Corporation Example 1 Production of Phenolic Hydroxyl Group-Containing Resin (1)

108.1 g of meta-cresol, 39.6 g of paraldehyde, 250 g of n-butanol, and 60 g of para-toluenesulfonic acid were put into a flask provided with a thermometer, a dropping funnel, a cooling tube, and a stirrer, and the resultant was heated to 100° C. and allowed to react for 10 hours under a reflux condition. After the reaction ended, 280 g of methyl isobutyl ketone was added thereto, and liquid-liquid separation washing was performed five times with 400 g of water. After the washing with water, methyl isobutyl ketone was distilled off from the organic layer by heating under reduced pressure, whereby a phenolic hydroxyl group-containing resin (1) was obtained. A GPC chart of the phenolic hydroxyl group-containing resin (1) is shown in FIG. 1, and an MS spectrum thereof is shown in FIG. 2. The weight average molecular weight (Mw) of the phenolic hydroxyl group-containing resin (1) was 1,847, and the residual amount of meta-cresol in the resin calculated from the GPC chart was 0.4%. In addition, it was confirmed by MS spectral analysis that a component corresponding to a compound of which the n value in the structural formula (1) is any of 4 to 14 is present. The content of the compound of which the n value in the structural formula (1) calculated from the GPC chart is 4 was 26.9%.

Example 2 Production of Phenolic Hydroxyl Group-Containing Resin (2)

122.2 g of 2,3-xylenol, 39.6 g of paraldehyde, 250 g of n-butanol, 60 g of para-toluenesulfonic acid were put into a flask provided with a thermometer, a dropping funnel, a cooling tube, and a stirrer, and the resultant was heated to 100° C. and allowed to react for 10 hours under a reflux condition. After the reaction ended, 280 g of methyl isobutyl ketone was added thereto, and liquid-liquid separation washing was performed five times with 400 g of water. After the washing with water, methyl isobutyl ketone was distilled off from the organic layer by heating under reduced pressure, whereby a phenolic hydroxyl group-containing resin (2) was obtained. A GPC chart of the phenolic hydroxyl group-containing resin (4) is shown in FIG. 3. The weight average molecular weight (Mw) of the phenolic hydroxyl group-containing resin (2) was 1,654, and the residual amount of xylenol in the resin calculated from the GPC chart was 1.7%. In addition, it was confirmed by MS spectral analysis that a component corresponding to a compound of which the n value in the structural formula (1) is any of 4 to 14 is present. The content of the compound of which the n value in the structural formula (1) calculated from the GPC chart is 4 was 43.2%.

Example 3 Production of Phenolic Hydroxyl Group-Containing Resin (3)

108.1 g of meta-cresol, 39.6 g of paraldehyde, 250 g of methanol, 60 g of para-toluenesulfonic acid were put into a flask provided with a thermometer, a dropping funnel, a cooling tube, and a stirrer, and the resultant was heated to 60° C. and allowed to react for 10 hours under a reflux condition. After the reaction ended, 280 g of methyl isobutyl ketone was added thereto, and liquid-liquid separation washing was performed five times with 400 g of water. After the washing with water, methyl isobutyl ketone was distilled off from the organic layer by heating under reduced pressure, whereby a phenolic hydroxyl group-containing resin (3) was obtained. The weight average molecular weight (Mw) of the phenolic hydroxyl group-containing resin (3) was 15,802, and the residual amount of meta-cresol in the resin calculated from the GPC chart was 0.1%. In addition, it was confirmed by MS spectral analysis that a component corresponding to a compound of which the n value in the structural formula (1) is any of 4 to 14 is present. The content of the compound of which the n value in the structural formula (1) calculated from the GPC chart is 4 was 9.3%.

Comparative Example 1 Production of Phenolic Hydroxyl Group-Containing Resin (1')

97.3 g of meta-cresol, 10.8 g of para-cresol, 57.2 g of 42% formalin, and 1 g of oxalic acid were put into a flask provided with a thermometer, a dropping funnel, a cooling tube, and a stirrer, and the resultant was heated to 100° C. and allowed to react for 3 hours. After the reaction ended, the temperature was raised to 200° C. under atmospheric pressure conditions, the pressure in the reaction system was reduced while maintaining at 200° C., and then distillation was performed for 4 hours, whereby a phenolic hydroxyl group-containing resin (1') was obtained. The weight average molecular weight (Mw) of the phenolic hydroxyl group-containing resin (1') was 12,500, and the residual amount of cresol in the resin calculated from the GPC chart was 0.5%.

Comparative Production Example 2 Production of Phenolic Hydroxyl Group-Containing Resin (2')

48 g of α-naphthol, 26 g of a 42% by mass formaldehyde aqueous solution, 50 g of isopropyl alcohol, and 9.4 g of 48% sodium hydroxide were put into a flask provided with a thermometer, a dropping funnel, a cooling tube, and a stirrer, and while blowing nitrogen gas thereinto, stirring was performed at room temperature. Thereafter, the temperature was raised to 80° C., and stirring was performed for 1 hour. After the reaction ended, the resultant was neutralized by adding 8 g of sodium phosphate monobasic, and cooled to separate crystals by filtration. The crystals were washed three times with 50 g of water and dried by heating under reduced pressure, whereby 47 g of a phenolic hydroxyl group-containing resin (2') was obtained.

Examples 4 to 6 and Comparative Examples 1 and 2

Various evaluation tests were performed on the photosensitive composition obtained by using each of the phenolic hydroxyl group-containing resins (1) to (3), (1'), and (2') obtained above in the following manner. The results are shown in Table 1. The phenolic hydroxyl group-containing resin (2') obtained in Comparative Production Example 2 was insoluble in propylene glycol monomethyl ether acetate, and thus, it was not possible to perform various evaluation tests thereon.

Evaluation of Heat Resistance 28 parts by mass of the phenolic hydroxyl group-containing resin was dissolved in 60 parts by mass of propylene glycol monomethyl ether acetate, and the resultant was filtered through a 0.2 μm membrane filter, whereby a composition for heat resistance tests was obtained. The composition was applied to be a thickness of about 1 μm on a 5 inch silicon wafer by a spin coater, and dried for 60 seconds on a hot plate at 110° C. The resin was scrapped from the obtained wafer, and the glass transition temperature (Tg) thereof was measured.

The measurement of the glass transition temperature (Tg) was performed using a differential calorimeter (DSC) (Q100 manufactured by TA Instruments) under conditions of a nitrogen atmosphere, a temperature range of –100° C. to 250° C., and a temperature-increase rate of 10° C./min.

Evaluation of Alkali Dissolution Rate

Formation of Coating Film 16 g of a phenolic hydroxyl group-containing resin was dissolved in 80 g of propylene glycol monomethyl ether acetate, then, 4 g of a photosensitive agent ("P-200" manufactured by Toyo Gosei Co. Ltd.) was added thereto, followed by mixing, and the resultant was filtered through a 0.2 μm membrane filter, whereby a photosensitive composition (a) was obtained. In the same manner, 16 g of a phenolic hydroxyl group-containing compound or a phenolic resin was dissolved in 80 g of PGMEA, then, the resultant was filtered through a 0.2 μm membrane filter, whereby a composition (b) not containing a photosensitive agent was obtained.

Each of the obtained compositions (a) and (b) was applied onto a silicon wafer having a diameter of 5 inches using a spin coater, and dried at 110° C. for 60 seconds, whereby a coating film (A) and a coating film (B) having a thickness of about 1 μm were obtained.

Measurement of Alkali Solution Dissolution Rate

The obtained coating films (A) and (B) were immersed in an alkali solution (2.38% by mass of a tetramethylammonium hydroxide aqueous solution) for 60 seconds, then, the film thickness after immersion was measured by a film thickness meter ("F-20" manufactured by Filmetrics Inc.), and the alkali dissolution rate (ADR) was evaluated. As the alkali solution dissolution rate is lower in the coating film (A) and the alkali solution dissolution rate is higher in the coating film (B), the resist composition has excellent developing properties. The resist composition exhibiting a lower alkali solution dissolution rate of the coating film (A) and a higher alkali solution dissolution rate of the coating film (B) is regarded as a resist composition having excellent developing properties.

Evaluation of Photosensitivity

The photosensitive composition (a) obtained above was applied to be a thickness of about 1 μm on a 5 inch silicon wafer by a spin coater, and dried for 60 seconds on a hot plate at 110° C. After a mask corresponding to a resist pattern of which the line-and-space was 1:1 and the lines having a width falling within 1 to 10 μm in increments of 1 μm was adhered onto the wafer, irradiation using a ghi line lamp ("multilight" manufactured by Ushio Inc.) was performed, and a heat treatment was performed under conditions of 140° C. and 60 seconds. Next, the resultant was immersed in an alkali developer (2.38% tetramethylammonium hydroxide aqueous solution) for 60 seconds, and dried for 60 seconds on a hot plate at 110° C.

The exposure amount (Eop exposure amount) at which the line width of 3 μm can be faithfully reproduced, in the case where the ghi line exposure amount was increased from 30 mJ/cm$^2$ in increments of 5 mJ/cm$^2$ was evaluated.

Evaluation of Resolution

The photosensitive composition (a) obtained above was applied to be a thickness of about 1 μm on a 5 inch silicon wafer by a spin coater, and dried for 60 seconds on a hot plate at 110° C. A photomask was mounted on the obtained wafer, irradiation with ghi line of 200 mJ/cm$^2$ was performed in the same manner as in the case of the alkali developing properties evaluation described above, and alkali development operation was performed. The pattern state was checked using a laser microscope ("VK-X200" manufactured by Keyence Corporation), and One that can be resolved at the L/S each having 5 μm was designated as "A", and one that cannot be resolved at the L/S each having 5 μm was designated as "B".

Evaluation of Base-Followability

The photosensitive composition (a) obtained above was applied to be a thickness of about 50 μm on a 5 inch silicon wafer by a spin coater, and dried for 300 seconds on a hot plate at 110° C. The surface of the obtained wafer was observed using a laser microscope ("VK-X200" manufactured by Keyence Corporation), and the case where there was no crack was designated as "A", and the case where there were cracks was designated as "B".

TABLE 1

|  |  | Example 4 | Example 5 | Example 6 | Comparative Example 1 | Comparative Example 2 |
|---|---|---|---|---|---|---|
| Phenolic hydroxyl group-containing resin |  | (1) | (2) | (3) | (1') | (2') |
| Heat resistance [° C.] |  | 110 | 112 | 164 | 91 | 177 (decomposition) |
| Alkali dissolution rate [angstrom/s] | Unexposed sample | A | A | A | A | — |
|  | Exposed sample | 6300 | 9800 | 3500 | 120 | — |

TABLE 1-continued

|  | Example 4 | Example 5 | Example 6 | Comparative Example 1 | Comparative Example 2 |
|---|---|---|---|---|---|
| Photosensitivity [mJ/cm$^2$] | 100 | 100 | 100 | 450 | — |
| Resolution | A | A | A | B | — |
| Substrate-followability | A | A | A | B | — |
| Etching resistance | A | A | A | B | — |

Examples 7 to 9 and Comparative Example 3

Various evaluation tests were performed on the curable composition obtained by using each of the phenolic hydroxyl group-containing resins (1) to (3) and (1') obtained above in the following manner. The results are shown in Table 2.

Preparation of Curable Composition 20 parts by mass of the phenolic hydroxyl group-containing resin and 1 part by mass of a curing agent ("1,3,4,6-tetrakis(methoxymethyl)glycoluril" manufactured by Tokyo Chemical Industry Co., Ltd.) were dissolved in 100 parts by mass of propylene glycol monomethyl ether acetate, and the resultant was filtered through a 0.2 μm membrane filter, whereby a curable composition was obtained.

Evaluation of Alkali Solubility

The curable composition obtained above was applied onto a 5 inch silicon wafer using a spin coater, and dried for 60 seconds on a hot plate at 110° C., whereby a sample with a resin film having a thickness of about 1 μm was obtained. The sample was immersed in an alkali developer (2.38% tetramethylammonium hydroxide aqueous solution) for 60 seconds. The film thickness before and after immersion was measured by a film thickness meter ("F-20" manufactured by Filmetrics Inc.), and the value obtained by dividing the difference by 60 was taken as the alkali developing properties [ADR (angstrom/s)].

Measurement of Dry Etching Resistance

The curable composition obtained above was applied onto a 5 inch silicon wafer using a spin coater, and heated for 60 seconds on a hot plate at 180° C. in an environment in which the oxygen concentration was 20% by volume, and further heated at 350° C. for 120 seconds, whereby a sample with a resin film having a thickness of 0.3 μm was obtained. The sample was subjected to an etching treatment using an etching apparatus ("EXAM" manufactured by SHINKO SEIKI CO., LTD.), under the following conditions, and the etching rate was calculated from the film thickness before the etching treatment and the film thickness after the etching treatment. The case where the etching rate was equal to or less than 150 nm/min was designated as "A", and the case where the etching rate was greater than 150 nm/min was designated as "B".

Etching Conditions

CF$_4$/Ar/O$_2$ (CF$_4$ 40 mL/min, Ar 20 mL/min, O$_2$ 5 mL/min)
Pressure: 20 Pa
RF power: 200 W
Treatment time: 40 seconds
Temperature: 15° C.

TABLE 2

|  | Example 7 | Example 8 | Example 9 | Comparative Example 3 |
|---|---|---|---|---|
| Phenolic hydroxyl group-containing resin | (1) | (2) | (3) | (1') |
| Alkali solubility [angstrom/s] | 5900 | 8800 | 3100 | 75 |
| Etching resistance | A | A | A | B |

The invention claimed is:

1. A phenolic hydroxyl group-containing resin, comprising:
a compound (A) having a molecular structure represented by the following Structural Formula (1):

[Chem. 1]

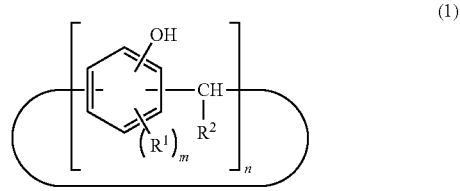

(1)

wherein R$^1$ represents an alkyl group, an alkoxy group, or an aryl group, R$^2$ represents an alkyl group, m is an integer of 1 to 3, and n is an integer of 4 to 6, provided that in the case where m is 2 or more, plural R$^1$'s may be the same as or different from each other.

2. The phenolic hydroxyl group-containing resin according to claim 1, comprising a compound (A-1) having a molecular structure represented by the following Structural Formula (1-1):

[Chem. 2]

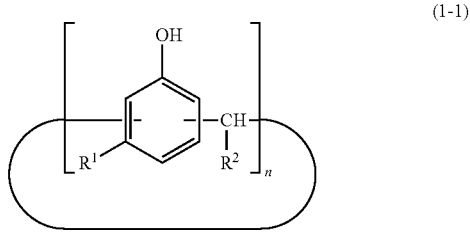

(1-1)

wherein R$^1$ represents an alkyl group, an alkoxy group, or an aryl group, R$^2$ represents an alkyl group and n is an integer of 4 to 6.

3. A photosensitive composition, comprising:
the phenolic hydroxyl group-containing resin according to claim 2; and a photosensitive agent.

4. A resist composition comprising the photosensitive composition according to claim 3.

5. A coating film formed of the photosensitive composition according to claim 3.

6. A curable composition, comprising:
the phenolic hydroxyl group-containing resin according to claim 2; and
a curing agent.

7. A cured product obtained by curing the curable composition according to claim 6.

8. A resist underlayer film obtained by curing the curable composition according to claim 6.

9. A photosensitive composition, comprising:
the phenolic hydroxyl group-containing resin according to claim 1; and a photosensitive agent.

10. A resist composition comprising the photosensitive composition according to claim 9.

11. A coating film formed of the photosensitive composition according to claim 9.

12. A curable composition, comprising:
the phenolic hydroxyl group-containing resin according to claim 1; and
a curing agent.

13. A cured product obtained by curing the curable composition according to claim 12.

14. A resist underlayer film obtained by curing the curable composition according to claim 12.

15. The phenolic hydroxyl group-containing resin according to claim 1, comprising a compound (A-2) having a molecular structure represented by the following Structural Formula (1-2):

[Chem. x]

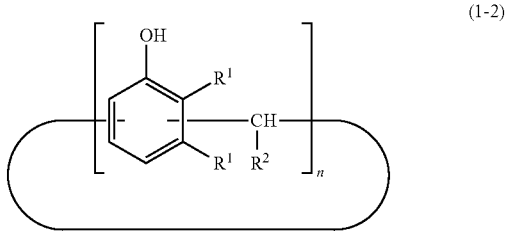

(1-2)

wherein R1 represents an alkyl group, an alkoxy group, or an aryl group, R2 represents an alkyl group, and n is an integer of 4 to 6.

16. A photosensitive composition, comprising:

the phenolic hydroxyl group-containing resin according to claim 15; and a photosensitive agent.

17. A resist composition comprising the photosensitive composition according to claim 16.

18. A coating film formed of the photosensitive composition according to claim 16.

19. A curable composition, comprising:

the phenolic hydroxyl group-containing resin according to claim 15; and a curing agent.

20. A cured product obtained by curing the curable composition according to claim 19.

* * * * *